United States Patent [19]

Keehn et al.

[11] Patent Number: 4,469,574
[45] Date of Patent: Sep. 4, 1984

[54] PROCESS AND AUTOMATED DEVICE FOR LASER-INDUCED CHEMISTRY

[75] Inventors: Philip M. Keehn, Newton; Robert M. Serino, Tewksbury, both of Mass.

[73] Assignee: Brandeis University, Waltham, Mass.

[21] Appl. No.: 380,631

[22] Filed: May 21, 1982

[51] Int. Cl.$^3$ .......................... B01J 19/08; B01J 19/12
[52] U.S. Cl. ........................ 204/158 R; 204/157.1 R; 422/186; 250/430; 250/433
[58] Field of Search .................... 204/157.1 R, 158 R, 204/157.1 L, 158 L, 193; 422/186.30, 186

[56] References Cited

U.S. PATENT DOCUMENTS

| | | | |
|---|---|---|---|
| 3,969,204 | 7/1976 | Neimann et al. | 422/186 |
| 4,042,334 | 8/1977 | Matovich . | |
| 4,097,384 | 6/1978 | Coleman et al. | |
| 4,176,024 | 11/1979 | Garbuny | 204/157.1 R |
| 4,199,419 | 4/1980 | Holyrod et al. | 422/186.3 |

Primary Examiner—Howard S. Williams
Attorney, Agent, or Firm—Hamilton, Brook, Smith and Reynolds

[57] ABSTRACT

This invention relates to an automated apparatus for use with electromagnetic radiation, such as a laser beam, to promote chemical reactions. The reaction chamber apparatus comprises a cylinder equipped with a reciprocating piston and with one or more windows. The invention also comprises an automated system which utilizes said chamber, and a method for utilizing the chamber and system. A laser beam enters the cylinder through one window, activates the reagents therein, and exits the chamber through a second window. After a mixture has been reacted, the laser is placed on standby, and the piston reciprocates, filling the cylinder with fresh reagent. Various embodiments are described which improve the efficiency of this invention.

17 Claims, 3 Drawing Figures

PROCESS AND AUTOMATED DEVICE FOR LASER-INDUCED CHEMISTRY

GOVERNMENT SUPPORT

The invention described herein was supported in whole or in part by a grant from the National Science Foundation.

DESCRIPTION

1. Technical Field

This invention is in the fields of chemical reaction vessels, automated controls, and lasers.

2. Background Art

Laser beams are useful for promoting chemical reactions, since they are capable of imparting a controllable amount of energy to a specific location or substance [1]. In order to maximize the yield of desired products, while minimizing the production of undesired by-products, lasers are used to introduce into a chemical system an amount of energy which is equal to, or slightly greater than, the activation energy of the desired reaction.

Carbon dioxide ($CO_2$) lasers are commonly used to activate chemical reactions [2]. Such lasers are capable of emitting infrared radiation in the wavelength range of 915 to 1093 $cm^{-1}$. The output may be tuned to obtain a beam of light with a desired wavelength. The energy contained within a photon of light is a function of the wavelength of the light, often expressed in terms of energy per mole of photons (kilocalories per $6.02 \times 10^{23}$ photons). By tuning a laser, the amount of energy per photon and the amount of energy per laser pulse may be carefully controlled.

The power output of $CO_2$ lasers can range from milliwatts/$cm^2$ to gigawatts/$cm^2$. $CO_2$ lasers may be operated in pulses, with a pulse duration that can range from about 1 to about 300 nanoseconds (ns), or in a continuous wave mode.

A laser-activated chemical reaction is usually conducted within a reaction chamber [3]. As used herein, a chamber may comprise any type of vessel, tank, container, or other device which is capable of temporarily holding one or more chemical substances. A reaction chamber must be equipped with at least one inlet through which one or more reagents may enter the chamber. At least one outlet must be provided; however, it is possible to design a reaction chamber which utilizes the same orifice as an inlet and an outlet. The laser beam must enter the chamber through material which is transparent to light of the desired wavelength. Various materials, such as potassium chloride (KCl), are transparent to infrared laser light or to light of other wavelengths. Such materials are suitable as window material provided that they resist chemical attack by the reagents, intermediates, and products involved in the reaction contained in the chamber. It is possible to create an entire chamber wall out of such transparent material, or to construct the walls of the chamber out of an opaque material fitted with one or more windows of transparent material. As used herein, the term window applies to any portion of a wall of a reaction chamber that is capable of transmitting radiation of one or more desired wavelengths.

If a laser beam with a given wavelength is not absorbed by one or more reagents, then a sensitizing molecule, such as silicon tetrafluoride ($SiF_4$), may may be used to drive the reaction [4]. The sensitizer is excited by the laser beam, thereby introducing energy into the reaction chamber. The energy is transferred to the reagents, thereby promoting the reaction.

DISCLOSURE OF THE INVENTION

This invention relates to an automated apparatus for use with electromagnetic radiation, such as a laser beam, to promote chemical reactions. It also relates to a method for using laser beams or other radiation to promote chemical reactions.

The apparatus of this invention comprises a system which includes and utilizes a reaction chamber. The reaction chamber comprises a piston and cylinder apparatus, which is equipped with the following components:

a. at least one inlet suitable for the passage of one or more chemicals into said chamber;

b. at least one outlet suitable for exhausting one or more chemicals from said chamber; and c. one or more windows arranged in the walls of said chamber which allow the radiation to enter the chamber, activate the chemicals therein, and exit from the chamber without impinging upon any component of said chamber that is not transparent to the beam of light.

The reaction chamber is one component of a system which comprises the following components:

a. said reaction chamber;

b. a source of electromagnetic radiation, such as a laser;

c. a drive mechanism which is capable of reciprocating the piston inside said chamber;

d. an inlet conduit for connecting the inlet of said chamber to a supply of reagent chemical;

e. means for controlling the flow of reagent chemical within said inlet conduit;

f. an outlet conduit for connecting the outlet of said chamber to a receptacle;

g. means for controlling the flow of chemical within said outlet conduit;

h. control means for causing the piston in said chamber to act in a synchronized manner with said source of electromagnetic radiation.

The method of this invention comprises the following steps. By means of a drive mechanism, a piston which is fitted within a cylinder is moved in a direction away from the cylinder head. This evacuates the cylinder and the movement of reagent(s) through one or more inlets into the cylinder. The piston is moved a sufficient distance so that it will not be impinged by a beam of electromagnetic radiation which passes through windows which are fitted in the walls of the cylinder. When the piston reaches this position, the cylinder contains reagent chemical(s). A laser beam (or other form of radiation) is then fired into the cylinder through at least one window. Energy is imparted by the laser to the reagent to promote a desired reaction. Unless the laser beam is fully absorbed by the chemicals in the cylinder, part of it will exit the cylinder through the opposing window. When the reaction reaches the desired degree of completion, or when the laser has operated for a desired amount of time, a control temporarily halts or redirects the firing of the laser. By means of the drive mechanism, the piston is moved in a direction toward the cylinder head. This forces the reaction product(s), and unreacted reagent(s), through the outlet into one or more receptacles. This completes a reaction cycle, which may be repeated any desired number of times.

There are numerous accessory devices and methods which can be used to aid the system in the conduct of various chemical reactions. Several such devices and methods are disclosed herein.

BEST MODE OF CARRYING OUT THE INVENTION

Figure 1:
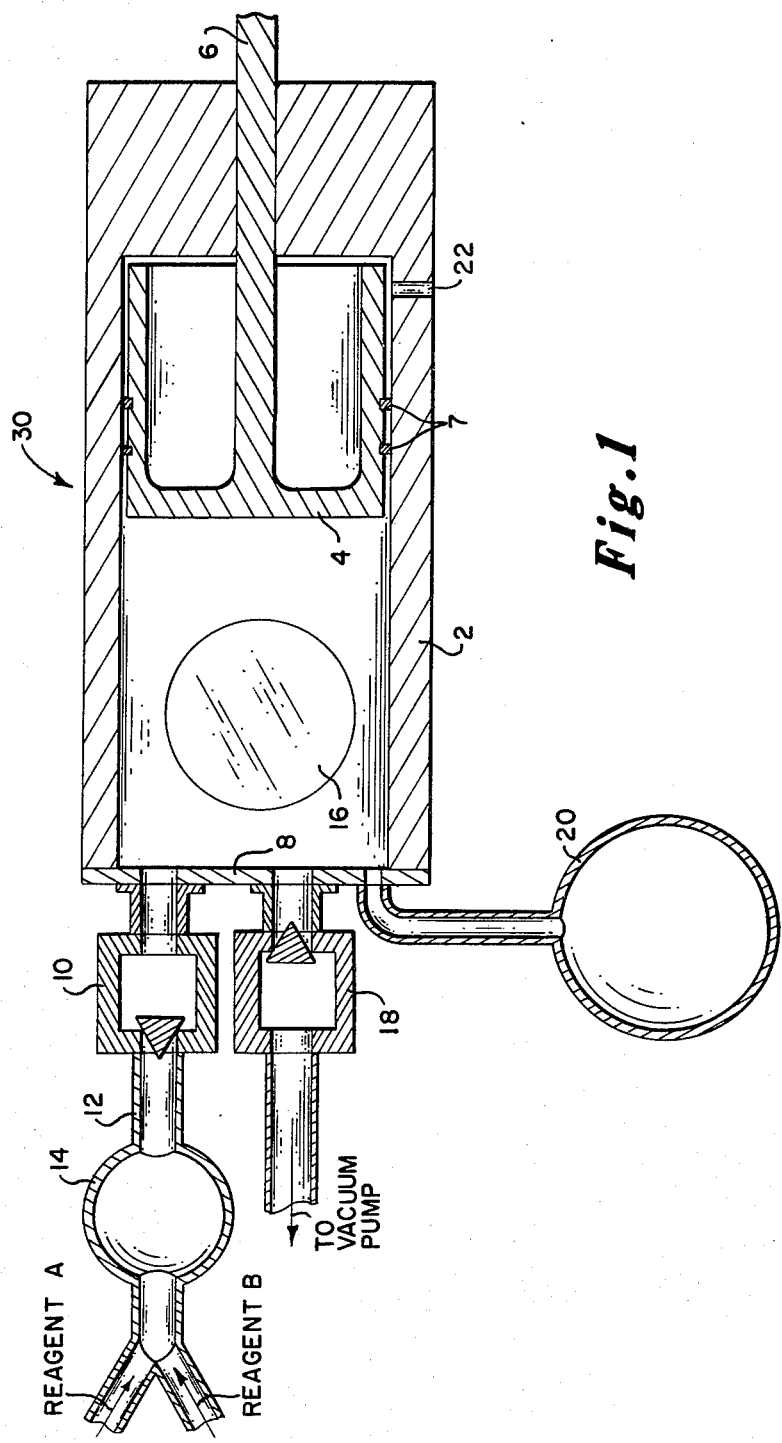
FIG. 1 illustrates a cross-sectional view of a reaction chamber of this invention.

One preferred embodiment of the reaction chamber of this invention comprises a piston and cylinder apparatus as shown in FIG. 1. In this figure, reaction chamber 30 comprises cylinder 2 and compatible piston 4, which is driven by piston rod 6. Piston 4 preferably is fitted with one or more elastomeric rings 7 to provide a pressure-tight seal between the piston side and the cylinder wall. At the start of a cycle, piston 4 is pressed against cylinder head 8, so that the volume of the reaction chamber is very small. Inlet valve 10 is opened, and piston rod 6 is operated by a drive mechanism (not shown in FIG. 1) to move piston 4 away from cylinder head 8. This creates a vacuum in cylinder 2, thereby drawing a reagent gas (indicated in FIG. 1 as Reagent A) from a reservoir (not shown), through inlet conduit 12 and inlet valve 10, into cylinder 2.

If an additional substance (designated as Reagent B), such a second reagent or a sensitizer such as silicon tetrafluoride, is to be involved in the reaction, it may enter cylinder 2 through inlet valve 10 or by a separate inlet valve (not shown).

In a preferred embodiment of this invention, inlet conduit 12 is equipped with feed chamber 14 which may promote mixing of reagents A and B before they enter the reaction chamber, and which may stabilize the flow of reagents into cylinder 2. For the purpose of mixing, feed chamber 14 may be equipped with one or more devices such as baffles, propellers, etc. For the purpose of flow stabilization, the feed chamber may be an accumulator which is connected by conduit to inlet conduit 12. Valves may be used to control the flow of reagents into feed chamber 14.

The system may be designed to cope with high or low pressures. The flow of reagents may be controlled by valves or other means to cause desired stoichiometric ratios of different reactants to enter cylinder 2.

After a desired quantity of reagent(s) have entered cylinder 2, the inlet valve(s) are closed, and a laser source commences operation. A laser beam with a desired intensity and wavelength enters the reaction chamber through window 16, which is made of a material that is transparent to the laser beam. The laser beam is absorbed by reagent or sensitizer molecules, causing a significant number of the reagent molecules to react and create one or more desired products.

Unless the laser beam is fully absorbed by the chemical(s) in the chamber, it will exit the chamber through a second window (not shown in FIG. 1). If the area of each window is larger than the cross-sectional area of the laser beam, the laser beam may be directed so that it will not strike any material other than the windows or the chemicals being reacted or produced. This avoids any undesired reactions that might occur if the laser impinges on a metallic or other surface in the presence of a reactive chemical.

If desired, a photodetector may be placed in the path of the exiting laser beam. Such devices can detect the number of laser pulses passing through the chamber, and the intensity of each pulse. This information may be used, for example, to add another pulse to a cycle if a misfire is detected. Alternately, such a device may be useful to evaluate the degree of completion of the reaction in the chamber, if the reaction product absorbs light of the laser wavelength substantially more or less than the reagents absorb the same wavelength.

There are a variety of other devices which can be used to automatically determine when the reaction has reached the desired degree of completion. For example, if the reaction is accompanied by a gain or loss in heat, pressure, acidity, humidity, or another variable, then one or more sensors can measure the degree of change of any relevant variables. Certain types of sensors are more appropriately placed inside the chamber, while other types of sensors are suitable for placement outside the chamber, as may be determined by those skilled in the art. Such sensors may generate an electronic or other signal which can be processed by a control unit to determine when to commence a new cycle.

When the reaction has reached the desired degree of completion, the control unit interrupts or redirects the laser source, e.g., by switching the laser to "standby" operation or by redirecting the beam to a different reaction chamber. Outlet valve 18 is opened, while inlet valve 10 remains closed. Piston rod 6 is driven causing piston 4 to approach cylinder head 8. This evacuates the chamber and forces the product(s), as well as any unreacted reagent(s) to exit cylinder 2 through outlet valve 18 into a receptacle or other device. As used herein, "receptacle" includes any device which is capable of holding, processing, or otherwise receiving material that is expelled from the reaction chamber. Such devices include condensation traps, filters, flasks or other containers, chambers for other reactions, etc.

After piston 4 has completed its motion, outlet valve 18 is closed and inlet valve 10 is opened. The reaction cycle may be repeated any number of times.

If desired, cylinder 2 may be fitted with condensation trap 20 to remove liquid droplets which may condense on the walls of cylinder 2. Such droplets may be forced into condensation trap 20 to remove liquid droplets which may condense on the walls of cylinder 2. Such droplets may be forced into condensation trap 20 by gravity and/or by the motion of piston 4 toward cylinder head 8.

Preferably, cylinder 2 is equipped with an orifice or conduit 22. This allows the back pressure on the piston to be controlled so that the pressure on both sides of the piston is approximately equal. If cylinder 2 is operated at a low pressure or high pressure, then conduit 22 should be connected to a vacuum pump or pressure pump, respectively. Depending upon a variety of factors, including pressure differentials involved, the power of the piston drive mechanism, the oscillating frequency of the piston and the integrity of the piston rings 7, different methods of backpressure control may be preferred for different reactions. For certain systems and reactions, it may be preferred to set the vacuum or pressure pump connected to conduit 22 at a single preset value. In such cases, temporary pressure differentials might not adversely affect the motion of the piston, and might act as "springs" to assist the reciprocation of the piston, especially if the reciprocation is relatively rapid. Alternatively, if the reciprocation of the piston is relatively slow, it may be preferred to synchronize the vacuum or pressure pump with the reciprocation of the piston to avoid a sustained pressure differential.

It is possible to control the atmosphere behind the piston, so that molecules which seep past piston rings 7 will not adversely affect the chemical reaction in the chamber. This may be done by flushing the backspace with inert gas, with one or more reagent chemicals, or with any other desired compound before the reaction is commenced. In addition, a vacuum or pressure pump which is coupled to conduit 22 may also be coupled to a reservoir of inert gas, reagent, or other compound.

Figure 2:
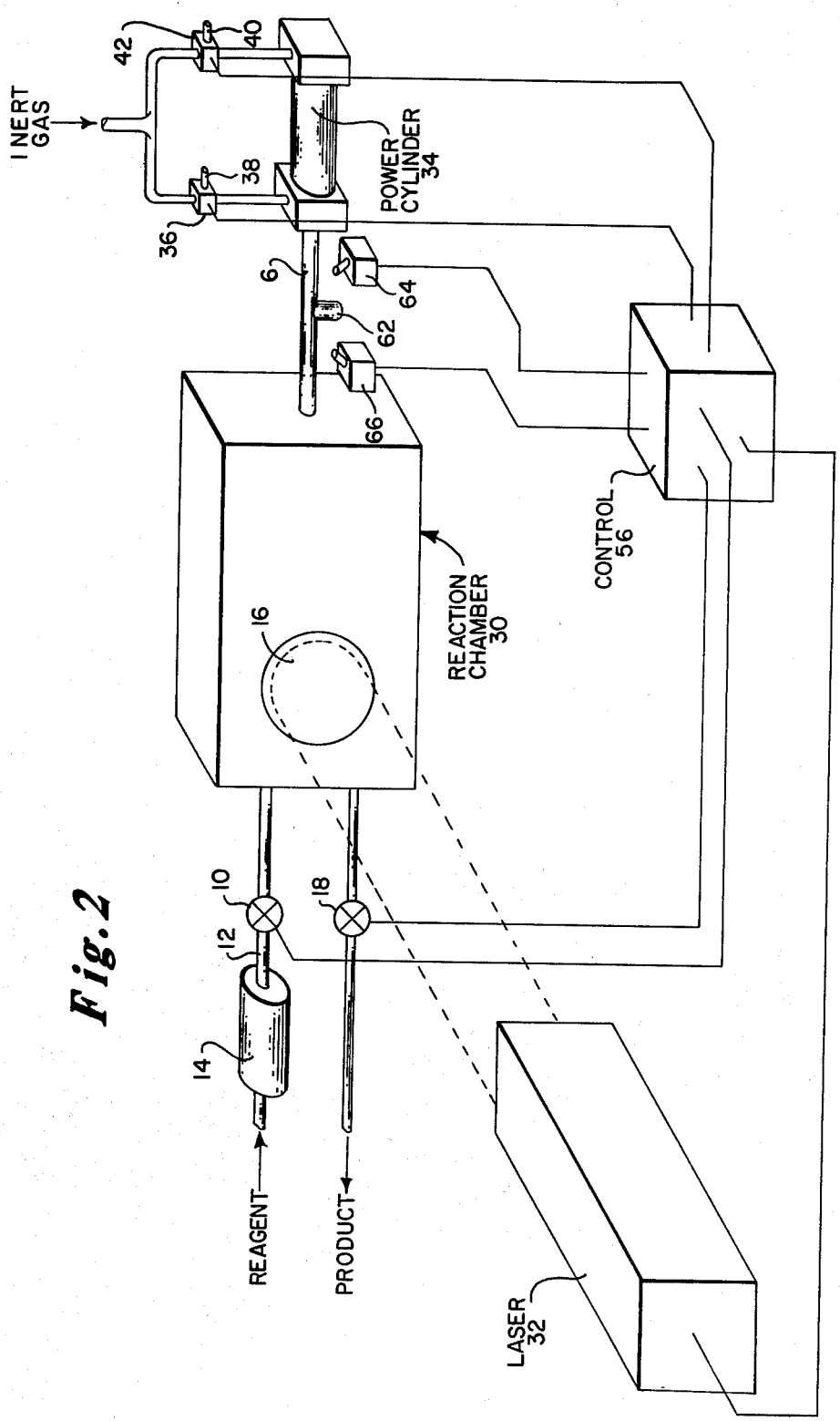
FIG. 2 illustrates a schematic view of the system of this invention.

FIG. 2 illustrates a system which contains a reaction chamber, such as reaction chamber 30 shown in FIG. 1 and described above. Laser 32 is aligned so that a laser beam shines into window 16, passes through chamber 30, and exits through a second window (not shown) on the opposite side of chamber 30. Piston rod 6 is connected to a piston inside chamber 30, and to a drive mechanism, such as an electric motor. In one preferred embodiment, shown in FIG. 2, the drive mechanism comprises a power cylinder 34. Cylinder 34 contains a piston which can be reciprocated by an inert gas, such as nitrogen. Such cylinders are commercially available, e.g., Model 6-BFD-3 made by Humphrey, Inc., Kalamazoo, MI. Each end of the cylinder is coupled to a 3-port valve, such as Model 8320B83 made by Automatic Switch Co., Florham Park, NJ. To enlarge the volume of chamber 30, gas is forced through valve 36 into power cylinder 34 causing a piston inside cylinder 34 to move. Gas inside cylinder 34 which is displaced by the movement of the piston inside cylinder 34, escapes through exhaust outlet 40 of valve 42. To reduce the volume of chamber 30, valve 36 is closed, exhaust nozzle 38 is opened, and gas is forced through valve 42 into cylinder 34.

In one embodiment of this invention, which is especially suitable for gaseous reagents, reaction chamber 30 is coupled to inlet valve 10, inlet conduit 12 and feed chamber 14. Inlet valve 10 and outlet valve 18 preferably are remotely operable valves, such as 2-port direct acting solenoid valves, such as Model 8262C2, Automatic Switch Co. Such valves are available in either normally closed (i.e., voltage is required to open them) or normally open (i.e., voltage is required to close them) configurations. Alternately, for certain uses, check valves which do not require remote activation could be suitable for use as inlet valve 10 and/or outlet valve 18.

The preceding discussion has been directed primarily toward reactions involving one or more gases. However, the chamber and system of this invention can be utilized to promote chemical reactions involving any phases or combustion of phases. Such reactions may require modifications to the devices or methods of this invention. For example, if a liquid reagent is to be used, the inlet to the chamber might be modified in various ways. For example, a heating element located at or near the inlet conduit may be utilized to vaporize one or more liquids. An atomizer at the inlet to the chamber may be utilized to disperse one or more liquids into small droplets within the chamber. If solid reagents are used, they may be dispersed in the chamber in powdered form or as an aerosol spray. The chamber may be operated in any position, e.g., vertical or horizontal.

The system must contain some type of control system; however, a wide variety of control systems can be utilized, each of which is likely to have both advantages and disadvantages.

One relatively simple system comprises a seesaw electronic solenoid with a manually adjustable time delay, shown as control 56 on FIG. 2. Such devices are commercially available, e.g., Model TDR-1060A1 made by Air-O-Tronics Products, Inc., Morrisville, NY 13408. This control unit can be coupled to the system in the following manner. Piston rod 6, as shown in FIGS. 1 or 2, can be equipped with spur 62. When chamber 30 is opened, spur 62 closes switch 64. This creates a signal which causes control 56 to close inlet valve 10 and begin firing laser 32. The laser continues firing for a predetermined period of time which is programmed into control 56. This time is preferably based upon previous experiments which determined the amount of laser energy required to drive a chemical reaction to an economically optimal degree of completion. When the laser has fired for the predetermined time, the control performs the following tasks:

a. switch laser 32 to standby;
b. open outlet valve 18 while inlet valve 10 remains closed;
c. open 3-port valve 42 while exhaust nozzle 40 remains closed, and open exhaust nozzle 38.

The pressure of the inert gas will then cause the piston in power cylinder 34 to move. This drives piston rod 6 and the piston inside chamber 30, forcing the product out of chamber 30 and into a receptacle. As the piston in chamber 30 approaches the cylinder head, spur 62 on piston rod 6 closes switch 66. This creates a signal which causes control 56 to perform the following tasks:

a. close outlet valve 18;
b. open inlet valve 10;
c. open exhaust nozzle 40;
d. open valve 36 while exhaust nozzle 38 remains closed.

Switches 64 and 66 may be spring-loaded or coupled to piston rod 6, allowing them to reset automatically during each cycle.

Alternately, the control system can receive and process signals from various types of sensors which can measure the degree of completion of the reaction.

There are numerous ways in which the system of this apparatus can be adapted to improve its efficiency. For example, the system can be designed for relatively rapid cycling, e.g., numerous cycles per second. For another example, one or more of the interior surfaces of the reaction chamber might be chilled to cause the product to condense and be removed from the path of the laser beam; this may be especially advantageous if the product will condense at a certain temperature at which the reagents remain gaseous.

Figure 3:
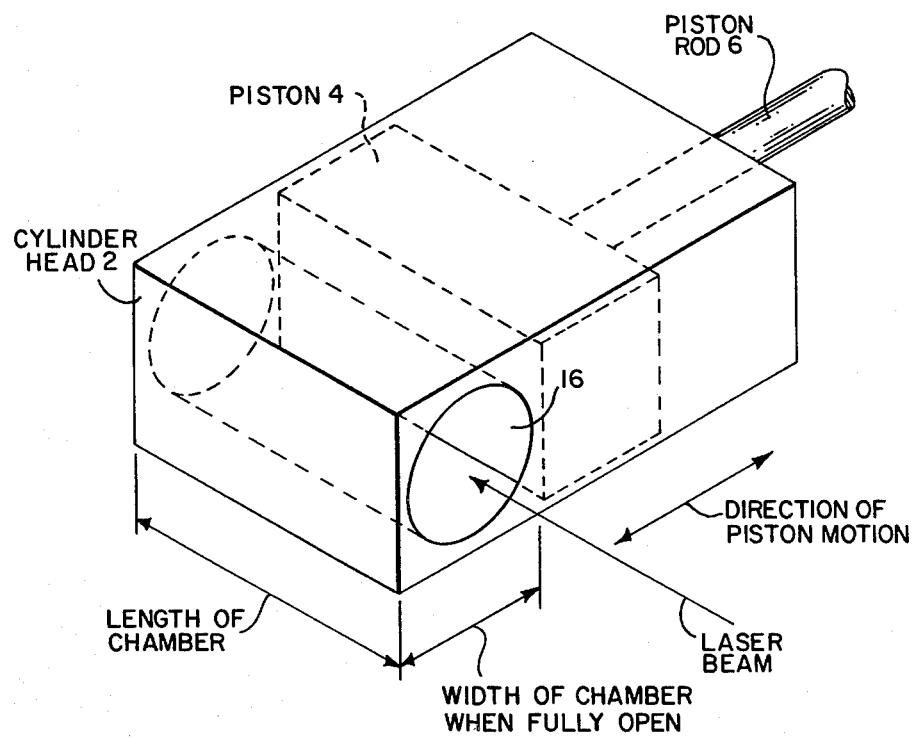
FIG. 3 illustrates one configuration of a reaction chamber which minimizes dead space.

As used herein, the term "cylinder" refers to any device, with one or more walls and a cylinder head, which contains a piston that is capable of reciprocal motion within the cylinder. In one preferred embodiment of this invention, the piston and cylinder are in a rectangular configuration as shown in FIG. 3. This allows for several advantages; in particular, the amount of "dead space" in the chamber (i.e., the volume of the chamber which is not in the path of the laser beam) is substantially reduced. Reagent molecules that swell in the dead space while a laser beam is passing through the chamber are not likely to react to form the desired product; therefore, dead space impedes the efficiency of the system.

The ratio of dead space to chamber volume can be reduced by increasing the length of the chamber. As used in this sense, "length" is measured along the path of the laser beam, as shown in FIG. 3. In general, increasing the length of the reaction chamber while maintaining a constant pressure means that more molecules will be impinged by the laser beam, and more of the energy of the laser beam will be absorbed by the reagents rather than pass through the entire chamber. The optimal length of a chamber will depend upon numerous factors (such as leakage of chemicals around the piston, force required to move the piston, mixing of the reagent within the chamber, power of the laser beam, etc.).

The amount of dead space can be reduced by minimizing the distance between one or more walls of said chamber and the path of the laser beam, and by minimizing the distance that the piston travels (i.e., the piston should stop moving a small distance after it is clear of the path of the laser beam). In other words, the width and the height of the chamber should be only slightly larger than the crossectional dimensions of the laser beam.

The shape and diameter of the laser beam may be controlled by various means, such as adjustable circular or square apertures. In addition, certain types of lasers emit laser beams with a square or rectangular cross-section; such lasers would be well-suited to use in systems of this invention.

This invention is not limited to the use of laser radiation to drive a chemical reaction. Other forms of electromagnetic radiation, such as ultraviolet radiation, X-rays and gamma rays, may also be used to drive specific chemical reactions utilizing the method and apparatus of this invention, as may be determined through routine experimentation by those skilled in the art.

The apparatus of this invention is well suited for using a variety of means for promoting or controlling chemical reactions. For example, one or more heating elements or cooling elements (such as metal tubes through which hot or cold fluids may flow) may be placed within the reaction chamber or embedded in one or more walls of the chamber, to promote chemical reactions which are aided by high or low temperatures. Other sources of energy, such as an ultrasonic transducer, may be placed inside the chamber to promote chemical reactions. Catalysts may be utilized in the chamber.

The piston head or a cylinder wall may be equipped with a device for stabilizing or otherwise controlling the pressure in the chamber during the reaction. A variety of stabilizing devices are known to those skilled in the art, such as a cushion chamber connected to the cylinder, or a spring-loaded pressure plate or an elastomeric diaphragm mounted in a cylinder wall or in the piston. A variety of other devices or methods are also known for varying the pressure inside the chamber during the reaction, such as altering the position of the piston in the cylinder.

The chamber and system of this invention have been utilized to conduct a variety of chemical reactions, such as the reactions described in the following example. These reactions were undertaken to demonstrate the feasibility of the system, and they do not reflect the optimal parameters or maximum efficiency that the system is capable of achieving.

EXAMPLE 1

Ethylacetate can be converted into acetic acid and ethylene according to the following formula:

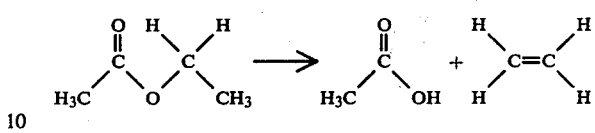

This reaction was conducted in the chamber and system of this invention, utilizing infrared laser radiation with a wavelength of 1054 cm$^{-1}$. The ethyl acetate was placed in the chamber at a pressure of 50 torr absolute. Each charge was irradiated with 14 pulses, at 4.88 joules/pulse. In one hour, 120 cycles were completed. 4.4 g of ethyl acetate produced 0.272 g of acetic acid and 0.127 g of ethylene.

Several other reactions which have been performed utilizing the chamber and system of this invention include:

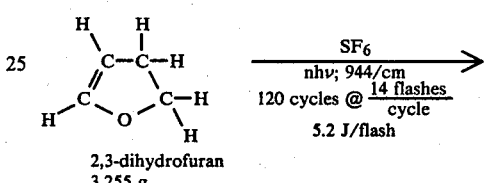

2,3-dihydrofuran
3.255 g

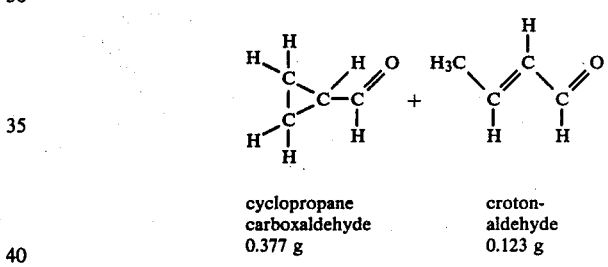

cyclopropane carboxaldehyde
0.377 g crotonaldehyde
0.123 g

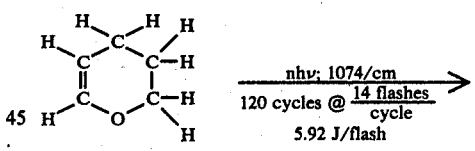

2,3-dihydropyran
4.49 g

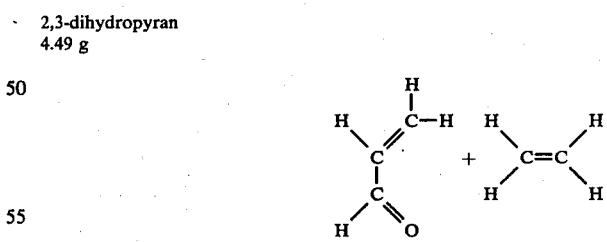

acrolein
0.288 g ethylene
0.144 g

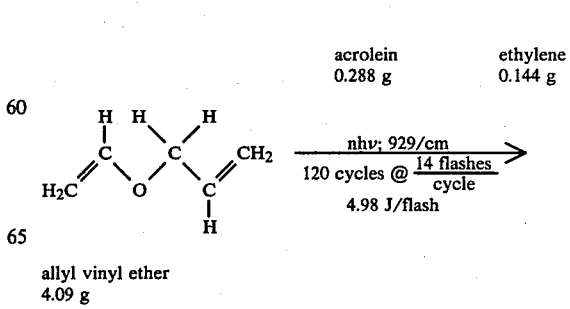

allyl vinyl ether
4.09 g

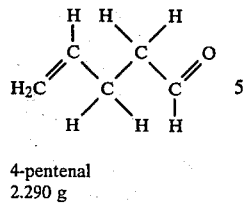

4-pentenal
2.290 g

Industrial Applicability

This invention has industrial applicability in the use of laser beams and other forms of radiation to promote chemical reactions. In particular, this invention is useful in reducing the amount of energy and reagents required to create a desired amount of a product, and to reduce the amount of waste and byproducts which result from chemical reactions.

Equivalents

Those skilled in the art will recognize, or be able to ascertain using no more than routine experimentation, many equivalents to the specific embodiments of the invention described herein. Such equivalents are intended to be encompassed by the following claims.

References

1. See, e.g., J. I. Steinfeld, ed., *Laser Induced Chemical Processes*, Plenum Press, N.Y., 1981; C. B. Moore, ed., *Chemical and Biochemical Applications of Lasers*, Academic Press, N.Y., 1974–1980.
2. See, e.g., E. Grunwald, D. F. Dever, P. M. Keehn, *Megawatt Infrared Laser Chemistry*, Wiley & Sons, N.Y., 1978.
3. See, e.g., J. S. Haggerty et al, "Sinterable Powders from Laser Driven Reactions," in Steinfeld, supra note 1, at page 165 et seq; U.S. Pat. No. 4,042,334 (Matovich 1977); D. Garcia et al, *J. Amer. Chem. Soc.* 100: p 6111 (1978); V. S. Letokhov, *Physics Today* 11: p 34 (1980).
4. See, e.g., K. J. Olszyna et al, *Tetrahedron Letters*, No. 19 p. 1609–1612 (1977).

We claim:

1. A chamber apparatus for promoting chemical reactions comprising:
   a. a chamber comprising a piston means enclosed in a cylinder for reciprocal movement within said cylinder, said piston means being able to traverse the volume of the cylinder, said cylinder having first and second end walls and a cylinder wall, the inner surfaces of said walls defining said chamber, and having at least one inlet for allowing one or more chemicals to enter said chamber, by movement of said piston means in a first direction, for reaction and at least one outlet for exhausting from said chamber one or more chemicals by movement of said piston in a direction opposite said first direction after said reaction has taken place; and
   b. at least one window comprising material which is transparent to electromagnetic radiation of one or more desired wavelengths, said window being arranged in a wall of said chamber for allowing a beam of electromagnetic radiation of a desired wavelength to enter said chamber to induce said chemical reaction.

2. An apparatus for promoting chemical reactions, comprising:
   a. a chamber apparatus, comprising
      (i) a chamber having enclosed piston means for reciprocal movement in said chamber and at least one inlet for allowing one or more chemicals to enter said chamber and at least one outlet for exhausting one or more chemicals from said chamber; and
      (ii) at least one window comprising material transparent to electromagnetic radiation, said window located in a wall of said chamber, for allowing a beam of electromagnetic radiation to enter said chamber to induce reaction of chemicals therein;
   b. a source of electromagnetic radiation;
   c. a drive mechanism for reciprocating said piston inside said chamber;
   d. an inlet conduit for connecting said inlet of said chamber to a supply of reagent chemical;
   e. means for controlling flow of reagent chemical within said inlet conduit;
   f. an outlet conduit for connecting the outlet of said cylinder to a receptacle;
   g. means for controlling the flow of chemical within said outlet conduit;
   h. a control means which for causing the piston in said cylinder to act in a synchronized manner with said source of electromagnetic radiation.

3. An apparatus of claims 1 or 2 wherein said cylinder is equipped with a condensation trap.

4. An apparatus of claims 1 or 2 wherein the area of each of said windows is larger than the cross-sectional area of said beam of electromagnetic radiation and the windows are arranged so that said beam of radiation can enter and exit said cylinder without impinging upon any component of said chamber that is not transparent to said beam.

5. An apparatus of claims 1 or 2 wherein said chamber is equipped with a sensor which is capable of indicating the degree of completion of a chemical reaction which occurs within said chamber.

6. An apparatus of claims 1 or 2 wherein said chamber is equipped with a feed chamber which enhances flow of chemicals into chamber thereby enhancing efficiency.

7. An apparatus of claims 1 or 2 wherein said chamber is equipped with means for controlling the pressure on both sides of the piston.

8. An apparatus of claims 1 or 2 wherein said chamber is equipped with one or more heating elements.

9. An apparatus of claims 1 or 2 wherein said chamber is equipped with one or more cooling elements.

10. An apparatus of claims 1 or 2 wherein said chamber is equipped with means for controlling the pressure in said chamber during a chemical reaction.

11. An apparatus of claims 1 or 2 wherein a means for introducing a desired type of energy is contained within said cylinder.

12. An apparatus of claims 1 or 2 wherein said piston has a piston face that that conforms to the internal shape of the chamber so as to minimize dead space within the chamber.

13. An apparatus of claims 1 or 2 wherein the distance between one or more walls of said chamber and the path of electromagnetic radiation is minimized such that the dead space within said chamber is minimal.

14. An apparatus of claims 1 or 2 wherein the distance travelled by said piston is minimized.

15. A method of promoting chemical reactions, comprising the following steps:
   a. placing one or more chemicals inside the chamber apparatus of claims 1 or 2;
   b. irradiating said chemicals with electromagnetic radiation thereby causing said chemicals to react and form one or more products; and
   c. removing said products from said chamber apparatus.

16. A method of promoting chemical reactions, comprising the following steps:
   a. expanding the volume of a reaction chamber, which comprises a piston and a cylinder which is equipped with one or more windows, by moving said piston within said cylinder, thereby causing one or more chemicals to enter said cylinder through an inlet;
   b. directing a beam of electromagnetic radiation through one or more of said windows into said cylinder, thereby irradiating said chemicals in said cyliner and causing said chemicals to react and form one or more products; and
   c. reducing the volume of said reaction chamber by moving said piston within said cylinder, thereby causing said products to be expelled from said cylinder into a receptacle.

17. In the method of using electromagnetic radiation to promote a chemical reaction, the improvement consisting of placing one or more chemicals in a reaction chamber which comprises a piston in a cylinder which is equipped with two or more windows by moving said piston within said chamber, directing electromagnetic radiation through one or more of said windows, thereby irradiating said chemicals in said cylinder and causing said chemicals to react and form one or more products; and reducing the volume of said reaction chamber by moving said piston within said cylinder, thereby causing said products to be expelled from said cylinder into a receptacle.

* * * * *